United States Patent [19]

Händel

[11] Patent Number: 4,735,779
[45] Date of Patent: Apr. 5, 1988

[54] METHOD FOR TESTING THE VISCOSITY OF SYNTHETIC RESINS AND APPARATUS FOR THE IMPLEMENTATION OF THE METHOD

[76] Inventor: Max D. Händel, Alte Siegburger Strasse 12, D-5204 Lohmar, Fed. Rep. of Germany

[21] Appl. No.: 845,700
[22] PCT Filed: Jul. 13, 1985
[86] PCT No.: PCT/EP85/00347
§ 371 Date: Mar. 17, 1986
§ 102(e) Date: Mar. 17, 1986
[87] PCT Pub. No.: WO86/00705
PCT Pub. Date: Jan. 30, 1986

[30] Foreign Application Priority Data
Jan. 17, 1984 [EP] European Pat. Off. .......... 8410841.5

[51] Int. Cl.$^4$ ............ G01N 33/44; G01N 30/96; G05D 23/00; L08F 2/00
[52] U.S. Cl. .................. 422/105; 526/59; 422/62; 422/108; 422/131; 436/85
[58] Field of Search ............ 526/59, 60, 61; 422/62, 422/108, 131, 105; 436/85

[56] References Cited

U.S. PATENT DOCUMENTS

| | | | |
|---|---|---|---|
| 2,989,517 | 6/1920 | Hanson et al. | 526/60 |
| 3,108,094 | 10/1963 | Morgan | 526/60 |
| 3,493,345 | 2/1970 | Windley . | |
| 3,503,937 | 3/1970 | Allen et al. | 526/59 |
| 3,787,359 | 1/1974 | Horn et al. | 422/131 |

Primary Examiner—Edward J. Smith
Assistant Examiner—Peter D. Mulcahy
Attorney, Agent, or Firm—Diller, Ramik & Wight

[57] ABSTRACT

An apparatus which includes a reaction vessel from which is tapped a sample of synthetic resin by a tap line, a feed pump in the tap line delivers the synthetic resin to a mixer, a heat exchanger and a viscosimeter, and the latter reflects end product characteristics of the main reaction vessel output. A solvent is also fed to the tap line between the feed pump and the static mixer, and the tap lie downstream of the viscosimeter can be selectively directed back to the reaction vessel, to a dilution container, or to a collection vessel.

11 Claims, 1 Drawing Sheet

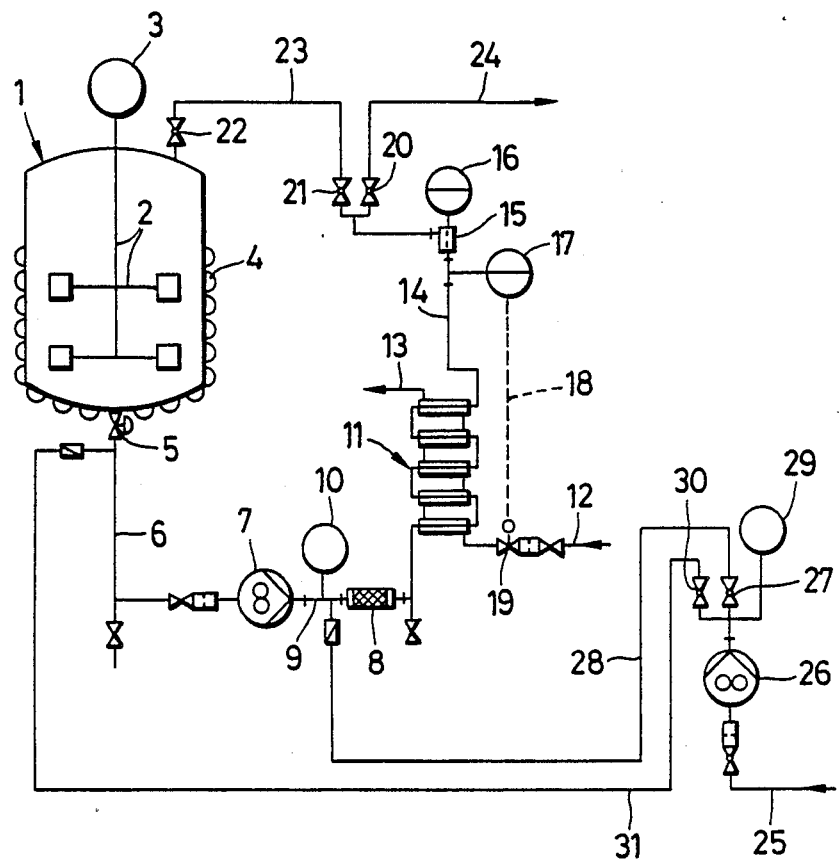

METHOD FOR TESTING THE VISCOSITY OF SYNTHETIC RESINS AND APPARATUS FOR THE IMPLEMENTATION OF THE METHOD

TECHNICAL FIELD

The invention relates to a method for testing the viscosity of synthetic resins during the manufacturing process of these synthetic resins in a reactor, with a slight partial flow of synthetic resin being withdrawn from the reactor.

STATE OF THE ART

The viscosity must be constantly monitored as a determinant parameter during the manufacture of synthetic resins. Presently the conventional procedure is to sample the reactor. Such samples then are examined in the lab and the test results determine the further process. Sampling and viscosity determination in the lab as a rule demand from a quarter to three-quarters of an hour. Because the viscosity rises especially ever more rapidly toward the end of the process, the delivery specifications can be exceeded on account of the time required to test the viscosity.

Another problem is incurred, namely that there is no clear relation between the viscosity of the flowing melt, ie of the product in the reactor, and that of the resin which corresponds to the delivery specifications, ie the final synthetic resin. This is the case especially where a solvent is added to the synthetic resin. This is a minor problem so long as macromolecular materials put together from sharply defined chemical raw substances, are involved. Illustratively this is the case for the manufacture of unsaturated polyesters. If on the other hand raw materials such as oils and fats are used in the manufacture of synthetic resins products, substantial problems are incurred. Almost in all cases there is absent an unambiguous relation between the viscosity of the flowing melt and the solvent viscosity, ie the viscosity of the end product. Also, even slight deviations in solvent composition may cause further deviations in the end product.

It is known per se furthermore that the solid content in synthetic solutions normally is between 50 and 70%. Accordingly when the viscosity is tested in the lab following sampling, dilution takes place in the same ratios, and the viscosity is then determined at a fixed temperature. The serial sampling is continued until the desired end specification is obtained. Thereupon the reactor process is interrupted, most of the time by cooling. Because of the repeated withdrawals of samples each requiring its own viscosity determination, it happens,—it can hardly be avoided, that the last point in the process is not reached or is exceeded, whereby deviations are incurred in the viscosity from that desired in the end product.

DESCRIPTION OF THE INVENTION

Beginning with the method initially discussed, whereby a small partial flow is withdrawn from the reactor and from which then samples are taken in the manner described and are tested, it is the object of the invention to create a method for viscosity testing allowing to determine the viscosity of the synthetic resin in the reactor at any time and without loss of time, and whereby furthermore an unambiquous relation may be established to the viscosity of the end product.

This object is solved by the invention in that the partial flow is tapped continuously and then is cooled to a constant temperature and is continuously fed thereupon to an in-line viscosimeter.

A preferred implementation of the method consists in feeding continuously a solvent at such a specified ratio to the partial flow in which it is then mixed that a match is obtained with respect to the end product, and in that thereupon cooling is undertaken.

Further advantageous implementations of the method of the invention are stated in the dependent claims 2 and 4 through 7.

The invention furthermore concerns apparatus to carry out the above discussed methods, with a reactor (reaction vessel) and with a tap line for a small partial flow of the synthetic-resin reactor contents and with a feed pump in the tap line, being characterized in that the tap line is provided with a heat exchanger acting as a cooler and in that as seen in the direction of flow, an in-line viscosimeter (viscosity tester) in present after the heat exchanger.

Further advantageous embodiments of the apparatus of the invention are stated in the dependent claims 9 through 15.

DESCRIPTION OF THE DRAWING

The drawing schematically shows an illustrative embodiment of the apparatus or plant of the invention. The invention is discussed below in greater detail in relation to this drawing.

The apparatus of the invention includes a reactor 1, i.e. a reaction vessel provided in manner known per se with a mixer system 2 driven by a motor 3. The casing and the bottom of the reactor are equipped with a heating and cooling system 4 shown in a simplified manner, which is also known per se. It should be borne in mind that the reactor furthermore is provided with omitted means for filling and emptying its contents in synthetic resin. A tap line 6 is hooked up to the lower reactor part by means of a valve and leads to a feed pump 7. The feed pump continuously withdraws a small partial flow of the reactor contents in synthetic resin and supplies it through a connecting line 9 to a heat-exchanger 11 acting as a cooler. The partial flow of the particular product is cooled in this heat exchanger 11 to a constant temperature depending on the particular kind of synthetic resin to be manufactured, for instance the cooling takes place from about 250° C. to about 50° C. The heat exchanger 11 is equipped with a first-runnings cooling water device 12 and a cooling water reflux device 13. In the cooling water pre-runnings device 12 is located a control valve 19 regulating the cooling to a constant temperature, for instance independently of the measuring site of the temperature testing and display device 17 by means of a control line 18 symbolically indicated in dashed lines.

Due to the feed pump 7, the partial flow passes in the cooled state through the line 14 into a viscosimeter 15 with a measuring pot. The viscosimeter or the viscosimeter testing equipment is provided with suitable testing and display devices shown in simplified manner and denoted by 16. It is essential that the viscosimeter 15 continuously measures, displays and records the viscosity of the partial flow of the particular contents of the synthetic-resin reactor and that such a measurement be used as a process-technological parameter for the automatic process-control of the reactor. If in particular the viscosity is determined in relation to the delivery specification, the process in the reactor may be interrupted by cooling this reactor. Following this continuous viscosity measurement, the partial flow can be made to pass through the valve 21, the line 23 and the valve 22 back into the reactor 1. As a whole a bypass is thus provided to the reactor.

Preferably the feed pump 7 is continuously adjustable so that a desired constant partial flow can be set.

In practice a solvent is generally added to the synthetic resin. Therefore an advantageous embodiment of the invention provides for continuously feeding a solvent in such a proportion to the tapped partial flow and mixing this solvent in it in such a manner that there will be agreement with the final product. After the solvent has been mixed with the partial flow, the already discussed cooling is carried out in the heat exchanger 11. Depending on the kind of synthetic resin, enough solvent is added so that the solid content in the solution of the synthetic resin ordinarily is between 50 and 70%. The temperature and the mixing ratio, ie the solid content of the partial flow, are continuously monitored and if necessary regulated. Whereas the partial flow of synthetic resin is fed without solvent, as explained above, back into the reactor after passing through the viscosimeter, the same feedback to the reactor may also be carried out if the partial flow of synthetic resin is mixed with a solvent because the relatively low proportion of solvent passing through the reactor practically leaves the reactor process unaffected; however in this case too it is possible to feed the partial flow mixed with solvent through the valve 20 and the line 24 into a dilution container or a collecting vessel.

As shown by the drawing, a solvent feed line with lines 25 and 28 is connected to the tap line 9 between the feed pump 7 and the heat exchanger 11. This solvent feed line is provided with its own metering pump 26. To achieve good mixing between the synthetic-resin partial flow and the solvent, the tap line 6, 9, 14 is provided with a stationary or static mixer 8. As shown in the drawing, this mixer 8 may be provided as a single unit between the hook-up site of the solvent feed line 28 and the heat exchanger 11. Another advantageous design provides the mixer in the form of a displacement body within the heat exchanger 11.

As already indicated above, the heat exchanger 11 is equipped with a temperature regulator shown in simplified manner and denoted by the reference numerals 17, 18 and 19. Furthermore pressure pickups 10 and 29 and also valves or stop cocks may be provided at suitable locations. Ordinarily the valve 27 is open so that a specific flow of solvent can be supplied by means of the metering pump 26 in continuous manner. Advantageously a rinsing line 31 with a valve whereby suitable opening and closing of the particular valves allows rinsing or cleaning the entire system of lines with solvents or other appropriate means.

In summary, it is important in the invention to achieve a rapid and continuous determination of viscosity. The continuous viscosity testing method of the invention does not measure the flowing melt viscosity in the reactor entailing the problems discussed above, but instead advantageously carries out the viscosity testing in a bypass to the reactor, the solid content, ie the synthetic resin in the reactor, and the solvent being mixed at a very specific mutual ratio, whereby agreement is provided with the end product, ie with the final product ready for delivery. Furthermore, as discussed, the mixture in the bypass is maintained at a constant temperature, with constant monitoring of the temperature, of the mixing ratio or the solid content. The viscosity is continuously measured, displayed, recorded and utilized as a process-technological parameter by means of the in-line viscosimeter in the bypass.

I claim:

1. Apparatus for measuring the viscosity of synthetic resins comprising a reaction vessel within which synthetic resin is processed, said reaction vessel including a main outlet for discharging the processed synthetic resin at a desired viscosity, means for continuously tapping a small partial flow of the synthetic resin from the reaction vessel, said continuous tapping means including a tap line in fluid communication with said reaction vessel, a feed pump for feeding the synthetic resin through said tap line downstream to heat-exchanger means for cooling the synthetic resin, viscosimeter means downstream of said heat-exchanger means for measuring the viscosity of the synthetic resin after passing beyond said heat-exchanger means, means for introducing a solvent into said tap line at a point between said feed pump and said heat-exchanger means, means for measuring the temperature in the tap line between the heat-exchanger means and the viscosimeter means, and means responsive to said temperature measuring means for controlling cooling fluid to said heat-exchanger means thereby matching the viscosity of the tap line synthetic resin to the desired viscosity of the discharged synthetic resin.

2. The apparatus as defined in claim 1 including means for selectively continuously adjusting the feed rate of said feed pump to thereby establish a desired flow rate of the synthetic resin through said tap line.

3. The apparatus as defined in claim 1 wherein said introducing means includes a metering pump for feeding the solvent to the tap line.

4. The apparatus as defined in claim 1 including means in said tap line between said feed pump and said heat-exchanger means for admixing the synthetic resin and solvent.

5. The apparatus as defined in claim 1 wherein said heat-exchanger means includes a mixer formed as a displacement body within said heat-exchanger means.

6. The apparatus as defined in claim 1 including a pair of lines connected to said tap line downstream of said viscosimeter means for selectively returning the tapped synthetic resin to said reaction vessel and a container, and valve means for controlling the flow of the tapped synthetic resin through said pair of lines.

7. The apparatus as defined in claim 4 including means for regulating the temperature of said said heat-exchanger.

8. The apparatus as defined in claim 4 including a pair of lines connected to said tap line downstream of said viscosimeter means for selectively returning the tapped synthetic resin to said reaction vessel and a container, and valve means for controlling the flow of the tapped synthetic resin through said pair of lines.

9. The apparatus as defined in claim 26 including a pair of lines connected to said tap line downstream of said viscosimeter means for selectively returning the tapped synthetic resin to said reaction vessel and a container, and valve means for controlling the flow of the tapped synthetic resin through said pair of lines.

10. The apparatus as defined in claim 4 wherein said introducing means includes a metering pump for feeding the solvent to the tap line.

11. The apparatus as defined in claim 10 including a pair of lines connected to said tap line downstream of said viscosimeter means for selectively returning the tapped synthetic resin to said reaction vessel and a container, and valve means for controlling the flow of the tapped synthetic resin through said pair of lines.

* * * * *